United States Patent
Kim et al.

(10) Patent No.: US 10,221,111 B2
(45) Date of Patent: Mar. 5, 2019

(54) METHOD FOR SEPARATING PROPYLENE FROM DEHYDROGENATION REACTION PRODUCTS OF PROPANE-CONTAINING FEEDSTOCK

(71) Applicant: SK GAS CO., LTD., Gyeonggi-do (KR)

(72) Inventors: Chul Jin Kim, Seoul (KR); Deuk Soo Park, Gyeonggi-do (KR); Kyung Min Kim, Gyeonggi-do (KR)

(73) Assignee: SK Gas Co., Ltd., Gyeongg-do (KR)

( * ) Notice: Subject to any disclaimer, the term of this patent is extended or adjusted under 35 U.S.C. 154(b) by 0 days.

(21) Appl. No.: 15/534,832

(22) PCT Filed: Dec. 4, 2015

(86) PCT No.: PCT/KR2015/013201
§ 371 (c)(1),
(2) Date: Jun. 9, 2017

(87) PCT Pub. No.: WO2016/093558
PCT Pub. Date: Jun. 16, 2016

(65) Prior Publication Data
US 2018/0265430 A1    Sep. 20, 2018

(30) Foreign Application Priority Data
Dec. 11, 2014 (KR) .................. 10-2014-0178410

(51) Int. Cl.
*C07C 7/13* (2006.01)
*C07C 7/12* (2006.01)
(Continued)

(52) U.S. Cl.
CPC .............. *C07C 7/12* (2013.01); *B01D 53/047* (2013.01); *B01D 53/0438* (2013.01);
(Continued)

(58) Field of Classification Search
CPC ..... C07C 7/13; C07C 11/02; B01D 2253/108; B01D 2253/116; B01D 2253/25; B01D 2253/308; B01D 2256/24; B01D 2257/7022; B01D 2259/4003; B01D 2259/40052; B01D 2259/40064;
(Continued)

(56) References Cited

U.S. PATENT DOCUMENTS

| 5,365,011 A | 11/1994 | Ramachandran et al. |
| 5,368,011 A * | 11/1994 | Bodner ............... F23C 3/00 126/110 R |
| 6,293,999 B1 * | 9/2001 | Cheng ............... B01D 53/0462 95/103 |

FOREIGN PATENT DOCUMENTS

| KR | 1020080114817 A | 12/2008 |
| KR | 1020120033368 A | 4/2012 |

OTHER PUBLICATIONS

International Search Report of PCT/KR2015/013201 dated Mar. 14, 2016.

* cited by examiner

*Primary Examiner* — Sharon Pregler
(74) *Attorney, Agent, or Firm* — Abelman, Frayne & Schwab

(57) ABSTRACT

An embodiment of this invention provides a method of effectively producing propylene by separating reaction products obtained by dehydrogenating propane-containing feedstock, using an adsorption process in lieu of conventional low-temperature separation processes.

17 Claims, 3 Drawing Sheets

(51) Int. Cl.
  *C07C 5/327* (2006.01)
  *C07C 11/06* (2006.01)
  *B01D 53/04* (2006.01)
  *B01D 53/047* (2006.01)
  *C07C 7/04* (2006.01)
(52) U.S. Cl.
  CPC ............... *C07C 5/327* (2013.01); *C07C 7/04* (2013.01); *C07C 11/06* (2013.01); *B01D 2256/24* (2013.01); *B01D 2257/7022* (2013.01); *B01D 2259/40013* (2013.01)
(58) Field of Classification Search
  CPC ........... B01D 2259/40079; B01D 2259/40081; B01D 2259/4009; B01D 2259/404; B01D 2259/41; B01D 53/0462; B01D 53/047; B01D 53/0476
  See application file for complete search history.

METHOD FOR SEPARATING PROPYLENE FROM DEHYDROGENATION REACTION PRODUCTS OF PROPANE-CONTAINING FEEDSTOCK

TECHNICAL FIELD

The present invention relates to a method of separating propylene from dehydrogenation products of propane-containing feedstock. More particularly, the present invention relates to a method of efficiently producing propylene by separating dehydrogenation products of propane-containing feedstock using a separation system including adsorption-desorption processing in lieu of a conventional separation manner using a low-temperature cooling system and a product splitter.

BACKGROUND ART

Light olefin such as ethylene, propylene, etc. is widely useful in the petrochemical industry, and is an important chemical material that is utilized as a building block for chemical products (oxo-alcohol, acrylonitrile, propylene oxide, butanol, acrylic acid, etc.) and plastic products (polypropylene, ethylene-propylene rubber, etc.). In particular, propylene is a colorless compound having a low boiling point and is typically trading in a polymer grade (purity of at least about 99.5%), a chemical grade (purity of about 90 to 96%) and a refinery grade (purity of about 50 to 70%).

Generally; such light olefin is obtained by subjecting naphtha or kerosene to pyrolysis (i.e. steam cracking) in the presence of water vapor. Although the demand for propylene is recently increasing, it is difficult to satisfy such high demand using a production process such as pyrolysis, and thus a variety of propylene synthesis methods (e.g. light fraction-catalytic cracking, etc.) are devised. The exemplary compositions (wt %) of the reaction products obtained through the above processes are shown in Table 1 below.

TABLE 1

|  | Reaction product of steam cracking | Reaction product of light fraction-catalytic cracking |
|---|---|---|
| Methane | 16.13 | 13.91 |
| Ethylene | 32.05 | 20.71 |
| Ethane | 2.91 | 8.93 |
| Propylene | 16.65 | 22.06 |
| Propane | 0.35 | 3.04 |
| $C_4$ | 10.94 | 8.97 |
| $C_5$ | 5.71 | 7.81 |
| $C_6$ or more | 14.18 | 13.58 |
| Others | 1.08 | 0.99 |

As a widely available process these days, a propylene preparation process using dehydrogenation of propane is known, and propylene is synthesized by Scheme 1 below.

(Scheme 1)

$$C_3H_8 \longrightarrow C_3H_6 + H_2$$

The dehyorogenation of propane is a process in which only propylene is selectively prepared from propane through a dehydrogecatioc reaction, and such a reaction is typically carried out for a short retention time through an endothermic reaction at a high temperature.

However, the propane dehydrogenation product is composed mainly of propylene, unreacted propane and hydrogen, and contains various byproducts. Thus, components having boiling points lower than that of a C3 gas mixture (propylene and propane) are conventionally separated through a low-temperature separation process (including a cooling process at about −100° C.), and the C3 gas mixture is split into propylene and propane through multi-tray distilation using a C3 product splitter. Here, in the C3 product splitter, propylene is removed as the overhead stream, and propane is removed as the bottom stream (e.g. U.S. Pat. No. 6,218,589).

In this regard, FIG. 1 shows a conventional process of separating and recovering propylene from the propane dehydrogenation product through a low-temperature separation process and using a C3 product splitter.

As shown in this drawing, the propane-containing feedstock is transferred into a feedstock evaporator 1 so as to mainly separate propane, which is then heated (a gaseous phase) by means of a reaction feedstock heater 2 and fed into a dehydrogenation reactor 3 at a high temperature, and is thus converted into a propylene-containing reaction product. This reaction product undergoes heat exchange in a heat exchanger (a steam producer) 4, is pressurized in a reaction product compressor 5, is transferred into a product gas dryer knock-out drum 7 via a heat exchanger 6, and is then separated based on the boiling point. The overhead stream (gas product; of the knock-out drum 7 is sequentially passed through a product gas dryer 8 and a first product gas chiller 9 as a cooling system and is then transferred into a deethanizer 10. On the other hand, the bottom stream (liquid product) of the knock-out drum 7 is transferred into a deethanizer 10 through a deethanizer feed dryer 11. Here, fractions having the lowest boiling points throughout the processing, such as hydrogen, methane and so on, are separated from the first product gas chiller 9, pressurized in a hydrogen compressor 17, and recovered as hydrogen and fuel gas in a hydrogen refiner 18.

In the deethanizer 10, the $C_2$ fraction is separated as the overhead stream, and fuel gas is recovered from she $C_2$ fraction by means of a second product gas chiller 12. Here, separation is easily performed using an ethylene refrigeration compressor 16. The bottom stream of the deethanizer 10 is transferred into a C3 product splitter 14 through a product dryer treatment bed 13. In the C3 product splitter 14, propylene is separated as the overhead stream, transferred into a propylene refrigeration compressor 15, subjected to heat exchange in she second product gas chiller 12, and then recovered as a final product. Propane is separated at the bottom of the C3 product splitter 14 and is then recycled into the feedstock evaporator 1.

Meanwhile, the bottom stream of the feedstock evaporator 1 is transferred into a deoiler 19 to thus be split into propylene and a $C_{4+}$ fraction. Here, the overhead fraction in the deoiler 19, namely propylene, is recovered into the feedstock evaporator 1, and the bottom fraction is transferred info a debutanizer 20. In she debutanizer 20, a $C_4$ fraction is separated at the top thereof, and a $C_{5+}$ fraction is separated at the bottom thereof.

In the aforementioned conventional techniques, a difference in boiling points of individual materials is used upon separation of the dehydrogenation products, and thus a low-temperature separation process (cooling at about −100 ° C.) using an excess of energy is performed to remove components having boiling points lower than that of the C3 gas mixture, Furthermore, as shown in Table 2 below, propylene and paraffin have similar boiling points and relatively volatile properties, and the C3 product splitter 14 has to have a large number of distillation trays (about 200).

TABLE 2

| Classification | Boiling point (° C.) | Note |
|---|---|---|
| Propylene | −47.8 | 1 atm |
| Propane | −42.1 | |

As described above, in the conventional method of separating the dehydrogenation products, the low-temperature separation process and the C3 product splitter need excessive energy, undesirably deteriorating processing efficiency. Thus, the development of energy-saving processes able to replace the low-temperature separation process and the C3 product splitter is required.

In order to replace the C3 product splitter, Korean Patent Application Publication No. 2012-0033368 discloses a process of separating propylene in which propylene is selectively adsorbed from a C3 mixture (a mixture of propane and propylene) among dehydrogenation products of propane and is separated from propane through displacement desorption using a desorbing agent. Specifically, this process (involving constant pressure or slight pressure fluctuations) is able to separate light olefin and paraffin without excessive pressure changes in the adsorber, in which olefin is selectively adsorbed to an adsorbing agent, and paraffin is passed, and is separated and recovered, via an additional still, and the adsorbed olefin is subjected to displacement desorption using a desorbing agent, and separated and recovered via an additional still.

Such a process is favorable because propylene and propane may be separated from each other at a constant pressure (or including slight pressure fluctuations) and at room temperature in lieu of the C3 product splitter required in the conventional techniques. Based on the results of research by the present inventors, however, when the above separation process is applied to the dehydrogenation products of propane, separation efficiency is decreased over time due to the deterioration of the adsorbing agent. Therefore, in order to separate tire dehydrogenation products of propane in the adsorption-displacement desorption manner, there is a need for methods of preventing the separation efficiency from decreasing due to the deterioration of the adsorbing agent.

DISCLOSURE

Technical Problem

An embodiment of the present invention is intended to provide a method of efficiently separating propylene from dehydrogenation products of propane-containing feedstock while reducing equipment investment and operation costs, compared to conventional methods using a low-temperature separation process and a C3 product splitter in which a large amount of energy is consumed upon separation of dehydrogenation products as described above. Similarly, in order to separate propylene from dehydrogenation products of propane-containing feedstock using an adsorption process, alternatives for the prevention of the deterioration of an adsorbing agent are required.

Accordingly, the present inventors have studied and ascertained that, among dehydrogenation products of propane-containing feedstock, byproducts including C4 olefin (especially isobutylene) have a great influence on the deterioration of an adsorbing agent in the downstream propylene separation processing unit through selective adsorption-displacement desorption of olefin.

An embodiment of the present invention is intended to provide a method of separating propylene from dehydrogenation products of propane-containing feedstock, including a process for preventing separation efficiency from decreasing due to the deterioration of the adsorbing agent and a separation process through the selective adsorption-displacement desorption of olefin.

Technical Solution

An embodiment of the present invention provides a method of separating propylene from a dehydrogenation product of propane-containing feedstock, comprising the steps of:

a) providing a propylene-containing product obtained by dehydrogenating the propane-containing feedstock, the propylene-containing product containing about 25 to 50 wt % of propylene, about 40 to 65 wt % of propane and about 1 to 8 wt % of a C4+ hydrocarbon;

b) transferring the propylene-containing product to a depropanizer so that at least a portion of the C4+ hydrocarbon is separated as the bottom stream and at first refined propylene-containing product is separated as the overhead stream;

c) transferring the first refined propylene-containing product to an adsorption separation unit so as to be split into (i) a propane-rich stream and (ii) a propylene-rich stream through the selective adsorption-desorption of olefin; and d) separating and recovering propylene from the propylene-rich stream.

In an exemplary embodiment, the amount of a C4 olefin compound (C4=) of the C4+ hydrocarbon in the propylene-containing product obtained in step a) may be about 0.5 to 3 wt % based on the amount of the propylene-containing product.

In an exemplary embodiment, the amount of isobutylene of the C4+ hydrocarbon in the propylene-containing product obtained in step a) may be about 0.1 to 2 wt % based on the amount of the propylene-containing product.

In an exemplary embodiment, the amount of 1,3-butadiene of the C4+ hydrocarbon in the propylene-containing product obtained in step a) may be about 0.01 to 0.2 wt % based on the amount of the propylene-containing product.

In an exemplary embodiment, the amount of benzene, toluene and xylene (BTX) of the C4+ hydrocarbon in the propylene-containing product obtained in step a) may be about 0.1 to 1 wt % based on the amount, of the propylene-containing product.

In an exemplary embodiment, pressurization and/or cooling may be further performed, before the transfer of the propylene-containing product obtained in step a) into the depropanizer, that is, before step b).

In an exemplary embodiment, separating, as the light gas stream, at least a portion of hydrogen, methane, a C2 hydrocarbon (ethane and ethylene), carbon monoxide and/or carbon dioxide may be further performed, before the transfer of the propylene-containing product into the depropanizer, that is, before step b).

In an exemplary embodiment, transferring the C4+ hydrocarbon separated as the bottom stream by the depropanizer to a debutanizer so as to be split, into a C4 hydrocarbon and a C5+ hydrocarbon may be further performed, and also, separating and recovering benzene, toluene and xylene (BTX) from the C5+ hydrocarbon may be further performed.

In an exemplary embodiment, the first refined propylene-containing product separated as the overhead stream by the depropanizer may contain hydrogen, methane, a C2 hydrocarbon and a C3 hydrocarbon, and may optionally further contain a small amount of C4+ hydrocarbon.

In an exemplary embodiment, before the transfer of the first, refined propylene-containing product separated as the overhead scream by the depropanizer to the adsorption separation unit, that is, before step c), a methylacetylene-propadiene hydrogenation reactor (MAPD converter) may be provided so that methylacetylene-propadiene (MAPD), not separated by the depropanizer, is removed through selective hydrogenation, thus producing a second refined propylene-containing product, which may then be supplied to the adsorption separation unit.

In an exemplary embodiment, the adsorption separation unit used in step c) may include at least two adsorbers connected in parallel and filled with an adsorbing agent.

In an exemplary embodiment, in order to prevent the deterioration of the adsorbing agent, a guard bed may be disposed upstream of the adsorption separation unit.

In an exemplary embodiment, separating propane from the propane-rich stream and recycling it to step a) may be further performed so that propane is dehydrogenated together with the propane-containing feedstock.

In an exemplary embodiment, the propane-rich stream may contain hydrogen, methane, and ethane, in addition to propane, and may further contain a desorbing agent.

In an exemplary embodiment, separating the desorbing agent from the propane-rich stream may be further performed so that a propane-rich stream having no desorbing agent is isolated, and supplying the desorbing agent separated from the propane-rich stream to step c) may be optionally further performed.

In an exemplary embodiment, splitting the propane-rich stream having no desorbing agent into hydrogen, fuel gas (methane and ethane) and propane through at least one process of distillation, PSA (pressure swing adsorption) and membrane separation may be further performed.

In an exemplary embodiment, the propylene-rich stream may contain ethylene in addition to propylene, and may further contain the desorbing agent.

In an exemplary embodiment, separating ethylene and the desorbing agent from the propylene-rich stream may be further performed. Here, supplying the separated desorbing agent to step c) may be further performed.

In an exemplary embodiment, removing water and/or a sulfur compound may be further performed after step a) (i.e. before step b)) and after step b) (i.e. before step c)) depending on the dehydration and desulfurization conditions of the downstream processing unit of step a).

Advantageous Effects

According to embodiments of the present invention, a method of separating propylene from dehydrogenation products of propane-containing feedstock is able to simply separate propylene and propane using an adsorber and a splitter having a small number of distillation trays without low-temperature separation and a C3 product splitter (requiring 200 or more separation trays), thereby reducing equipment investment costs and increasing energy efficiency. In particular, a depropanizer is disposed upstream of the processing unit for adsorption separation of propylene from the dehydrogenation products of propane-containing feedstock, thus preventing the adsorbing agent from deteriorating during the separation of propylene and propane, whereby the separation efficiency can be maintained high for a long period of time. Hence, the method of the invention is expected to be widely applied in the future.

Figure 1:
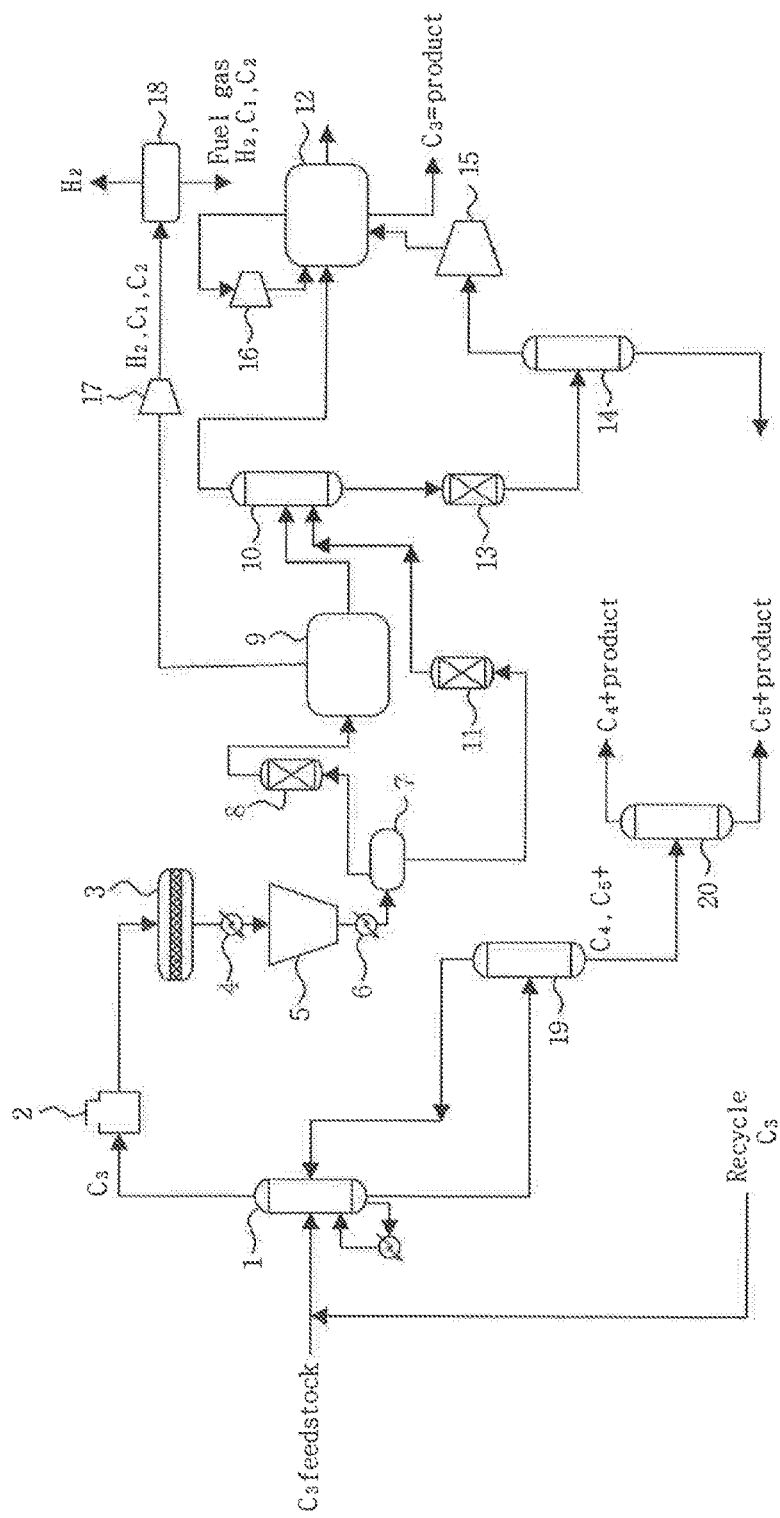
FIG. 1 shows a conventional process of separating propylene from a dehydrogenation product of propane-containing feedstock.

DESCRIPTION OF THE REFERENCE NUMERALS OF THE DRAWINGS 1, 101: feedstock evaporator 2, 102: feedstock heater
3, 103: dehydrogenation reactor 4: heat exchanger (steam producer)
5, 105: reaction product compressor 6: heat exchanger
7, 106: reaction product dryer knock-out drum 8, 107: product gas dryer
9: first product gas chiller 10: deethanizer
11: deethanizer feed dryer 12: second product gas chiller
13: product dryer treatment bed 14: C3 product splitter
15: propylene refrigeration compressor 16: ethylene refrigeration compressor
17: hydrogen compressor 18: hydrogen refiner
19: deoiler 20: debutanizer
104: compressor suction drum 108: depropanizer
109: olefin adsorption-desorption unit 110: desorbing agent drum
111: propane splitter 112: ethylene splitter
113: propylene splitter 114, 115: propane/hydrogen refiner Best Mode Exemplary embodiments of the present invention may be understood through the following description. The following description should be understood to explain specific embodiments of the present invention, and the present invention is not necessarily limited thereto.

Furthermore, the appended drawings are provided for clarity, and the present invention is not limited thereto, and details of the individual components thereof may be properly understood by the specific effects of the relevant description, which will be described later.

The terms used herein are defined as follows.

The term "depropanizer" refers to a column configured such that a hydrocarbon having 3 or fewer carbon atoms is separated from a mixture containing a hydrocarbon having 3 or more carbon atoms.

The term, "debutanizer" refers to a column configured such that a hydrocarbon having 4 or fewer carbon atoms is separated from a mixture containing a hydrocarbon having 4 or more carbon atoms.

The term "C4+ hydrocarbon" refers to a hydrocarbon having 4 or more carbon atoms.

The term "PSA" refers to a process of separating a multi-component gas mixture containing at least two gases having different adsorption properties. Here, the gas mixture is separated in a manner in which the gas mixture passes through an adsorption zone under pressurization conditions, whereby a specific gas component thereof is selectively adsorbed, the other gas components are passed through the adsorption zone, and the adsorbed gas component is desorbed under decompression conditions, thereby separating multiple gases.

The term "membrane separation" refers to a process of separating a gas mixture based on a difference in diffusion coefficient between gas components through the membrane.

The term "rich" means that a specific component or compound in the corresponding stream is contained in an amount of, for example, at least about 30 mol %, particularly about 50 mol %, more particularly at least 70 mol %, and at least 90 mol % in some cases. More broadly, the specific component in the stream fed into a predetermined separation process may be separated and discharged in an amount of at least 80%, and particularly at least 90%, into the corresponding stream separated by the predetermined, separation process.

Propane-Containing Feedstock

According to an embodiment of the present invention, the propane-containing feedstock may be composed exclusively of propane, but is typically derived from LPG. Specifically, the propane-containing feedstock may be a propane-rich LPG fraction derived from natural gas plants, or may be obtained as a byproduct of a refinery process, for example, hydrocracking or FCC processing. The amount of propane in the propane-containing feedstock may be, for example at least 70 wt %, particularly at least about 80 wt %, more particularly about 90 wt %, and yet particularly at least about 93 wt %.

Dehydrogenation

Propane of the propane-containing feedstock is converted into propylene as represented by Scheme 1 in the dehydrogenation reactor. Widely known propane dehydrogenation processes include Catofin® processing by Lummus Technology, Oleflex™ processing by UOP, and POH processing by Linde/BASF. The dehydrogenation reaction is typically carried out in the presence of a catalyst, and examples of the catalyst may include a platinum-tin/alumina catalyst, a chromium oxide/alumina (or zirconium) catalyst and the like.

For example, a Catofin® dehydrogenation process is carried out in a fixed-bed insulation reactor using a chromium, oxide (containing an alkali co-catalyst)/alumina catalyst (chromium oxide content: about 18 to 20 wt % and alkali metal content: about 1 to 2 wt %), and an Oleflex™ dehydrogenation process is conducted in a fluidized-bed insulation reactor using a Pt-Sn/alumina catalyst.

The dehydrogenation reaction may be carried out at, for example, about 500 to 700° C. (typically about 550 to 650° C., and more typically about 580 to 620° C.), but the present invention is not limited thereto. The dehydrogenation reaction may be performed using multiple reactors. In this case, individual reactors are connected in parallel, and continuous operation may be implemented in a manner in which, when the dehydrogenation reaction is carried out in a predetermined reactor, a recycling process is performed in the remaining reactor.

By the dehydrogenation reaction, propane in the feedstock is converted into propylene, thus obtaining a propylene-containing product, which includes not only propylene but also unreached feedstock and various byproducts. For example, the propylene-containing product obtained by dehydrogenation may include hydrogen ($H_2$), water ($H_2O$), methane ($CH_4$), acetylene ($C_2H_2$), ethylene ($C_2H_4$), ethane ($C_2H_6$), methyl acetylene (MA, $C_3H_4$), propadiene (PD, $C_3H_4$), propylene ($C_3H_6$), propane ($C_3H_8$), butadiene ($C_4H_6$), isobutylene (i-$C_4H_8$), 1-butene (1-$C_4H_8$), c-2-butene, t-2-buene, pentene, benzene, toluene, xylene, etc.

In an exemplary embodiment, at least a portion of the propylene-containing product obtained through the dehydrogenation reaction may be purged using a purging gas comprising a steam gas and/or an inert gas such as nitrogen and may then be transferred to the downstream processing unit. The propylene-containing product, may further include, as impurities, purging gas and byproducts due to side reactions involving the purging gas. Accordingly, the propylene-containing product may contain, for example, water ($H_2O$), nitrogen ($N_2$), carbon monoxide (CO), and carbon dioxide ($CO_2$). The amounts of such components, which may be included through purging, may vary depending on the kind of purging gas and the reaction conditions, including the reaction/purging time, and thus are difficult to determine as fixed values. Furthermore, the propylene-containing product obtained through a dehydration reaction may contain, as impurities, at sulfur compound included in the propane-containing feedstock, and a sulfur compound used to increase heat capacity during the dehydration reaction and to coat the inside of the reactor.

Specifically, the propylene-containing dehydrogenation product may contain, for example, about 25 to 50 wt % (particularly about 30 to 45 wt %) of propylene, about 40 to 65 wt % (particularly about 45 to 60 wt %) of propane, arid about 1 to 8 wt % (particularly, about 1.5 to 5 wt %) of a C4+ hydrocarbon. Furthermore, a C3 compound having a triple bond or two double bonds in the molecular structure thereof, such as methylacetylene-propadiene (MAPD), may be contained in a very small amount (e.g. about 500 wppm or less), In an exemplary embodiment, the amount of a C4 olefin compound (e.g. isobutylene, 1-butene (1-$C_4H_8$), c-2-butene, t-2-butene or the like) of the C4+ hydrocarbon in the propylene-containing product may be about 0.5 to 3 wt % (particularly about 1 to 1.5 wt %) based on the amount, of the propylene-containing product. In particular, the amount of isobutylene may be about 0.1 to 2 wt % (particularly about 0.5 to 1.5 wt %). Also, the amount of 1,3-butadiene of the C4+ hydrocarbon in the propylene-containing product may be, for example, about 0.01 to 0.2 wt % (particularly, about 0.03 to 0.1 wt %) based on the amount of the propylene-containing product, and the amount of BTX may be, for example, about 0.1 to 1 wt % (particularly, about 0.15 to 0.7 wt %) based on the amount of the propylene-containing product.

Separation of Dehydrogenation Product using Depropanizer

In an embodiment, the C4 olefin component of the propylene-containing product, especially isobutylene, affects the downstream adsorption-desorption unit. Particularly, isobutylene has no great influence on conventional separation processes using a cooling separation process and a product splitter, but significantly affects the adsorbing agent in the downstream isobaric adsorption separation unit.

Although the present invention is not bound to any specific theory, the above component disturbs displacement desorption after adsorption using the adsorbing agent, in a propane-propylene separation adsorber filled with a zeolite adsorbing agent. (for example, zeolite X or Y), or causes undesirable side reactions (for producing oligomers such as dimers and trimers, and naphthalene-based cokes having higher molecular weight). In this way, when the above component is fed into the zeolite-loaded adsorber, the performance of the adsorbing agent for selectively adsorbing propylene may be drastically deteriorated, thereby reducing the lifetime thereof.

Figure 2:
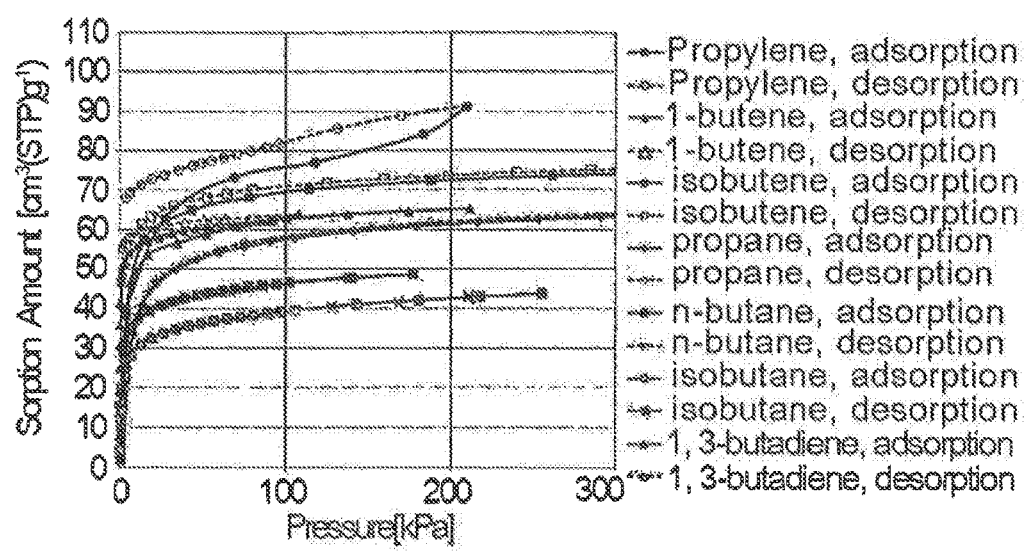
FIG. 2 shows changes in adsorbed amounts of propane, propylene, 1-butene, isobutene, n-butane, isobutane and butadiene (1,3-butadiene) through adsorption (pressurization) and desorption (decompression; using zeolite 13X among adsorbing agents usable in an adsorption separation unit.

FIG. 2 shows changes in the adsorbed amounts of propane, propylene, 1-butene, isobutene, n-butane, isobutane and butadiene (1,3-butadiene) through adsorption (pressurization) and desorption (decompression) using zeolite 13X, among adsorbing agents usable in the adsorption separation unit.

Referring to this drawing, as for propane, propylene, n-butane and isobutane, the adsorbed amount approximates zero with a decrease in pressure in the desorption curve (empty symbols). This means that propane, propylene, n-butane and isobutane are physically adsorbed to zeolite 13X, and most of the adsorbed components may be desorbed and are thus reversible. On the other hand, as for 1-butene, isobutylene (isobutene) and butadiene (1,3-butadiene), the adsorbed components are not desorbed, and are present even though the pressure approximates zero. Among components such as 1-butene, isobutylene (isobutene) and butadiene (1,3-butadiene), some of the adsorbed components still remain on the surface of the adsorbing agent due to chemical adsorption, and are thus regarded as deteriorating the performance of the adsorbing agent. Especially, isobutylene (isobutene), the desorption of which is most difficult, may have a significant effect on deterioration of the adsorbing agent.

In an embodiment of the invention, taking into consideration the effects of individual components of the dehydrogenation product on the subsequent propane-propylene separation process (an olefin adsorption-desorption unit) in an olefin adsorption-displacement desorption manner, a depropanizer is disposed upstream of the olefin adsorption-desorption unit so that at least a portion of the C4+ hydrocarbon is separated, as the bottom stream and a first refined propylene-containing product (containing a C3 or smaller hydrocarbon and hydrogen) is separated as the overhead stream. When the depropanizer is disposed upstream of the adsorption-desorption unit in this way, double-bond compounds (olefin and diolefin) in the C4+ hydrocarbon, and BTX components, especially isobutylene, may be substantially removed. Here, the amounts of propylene and propane in the overhead stream (first refined propylene-containing product) of the depropanizer may be, for example, about 30 to 50 wt % (particularly about 35 to 45 wt %) and about 40 to 65 wt % (particularly, about 45 to 60 wt %), respectively. The amount of isobutylene may be about 0.3 wt % or less (particularly, about 0.2 wt % or less, and more particularly about 0.1 wt % or less). The overhead stream (first refined propylene-containing product) of the depropanizer may contain not only propylene and propane but also hydrogen, C1 and C2 hydrocarbons, and other C3 hydrocarbons. Furthermore, the first refined propylene-containing product may also contain, as impurities, water, nitrogen, carbon monoxide and/or carbon dioxide.

In a specific embodiment, at least about 70% (particularly, at least about 80%, and more particularly about 90%) of the isobutylene in the propylene-containing product obtained through the dehydrogenation reaction is separated as the bottom stream of the depropanizer. As described above, in the case where the amount of isobutylene is not lowered to a predetermined level or less by means of the depropanizer, the introduction of isobutylene into the inlets of zeolite pores is further limited compared to other olefin compounds (1-butene, etc.), and thus, during the adsorption-desorption process, oligomerization and/or polymerization of isobutylene may significantly occur on the outer surface of zeolite crystals, thus remarkably increasing the deterioration of the adsorbing agent.

Also, by means of the depropanizer, the amounts of the diolefin component such as 1,3-butadiene and the BTX component may be lowered to about. 500 wppm or less (particularly about 300 wppm or less, and more particularly about 100 wppm or less) and about 100 wppm or less (particularly about 50 wppm or less, and more particularly about 30 wppm or less), respectively, in the overhead stream (first refined propylene-containing product) of the depropanizer.

Among the variety of components present in the propane dehydrogenation product in the present embodiment, most predetermined components that adversely affect the downstream adsorption separation unit may be removed all at once by disposing the depropanizer upstream of the adsorption separation unit. Furthermore, the amount of the C4 olefin component (especially, isobutylene) present in the propylene-containing product fed into the downstream adsorption separation unit is maintained at a predetermined level or less, whereby the purity of propane gas to be subsequently recycled may be improved to be equal or superior to that when using the conventional cooling separation system.

The operation conditions of the depropanizer are not particularly limited, so long as the above functions are performed, and may include, for example, a temperature of about 50 to 100° C. (particularly about 55 to 90° C.) at the top thereof, a temperature of about 120 to 150° C. (particularly, about 130 to 140° c.) at the bottom thereof, and a pressure of about 20 to 40 kg/cm$^2$ (particularly about 25 to 35 kg/cm$^2$). Here, the number of trays may be, for example, about 100 so 170, and particularly about 130 to 160. In this way, before the transfer of the dehydrogenation product into the adsorption separation unit for propane-propylene separation, the depropanizer is provided so as to preemptively remove the C4+ fraction (particularly C4+ olefin and diolefin, and BTX), especially isobutylene, from the propylene-containing product, thereby minimizing the effect thereof on the adsorbing agent used in the downstream adsorption-desorption unit.

Meanwhile, among the above byproducts, methylacetylene-propadiene (MAPD), corresponding to the C3 hydrocarbon, may not be removed by the depropanizer, but may be present in a very small amount in the propylene-containing product, and a portion thereof may be contained in the C4+ fraction separated as the bottom stream during the separation process using the depropanizer, and may onus have no great influence on the downstream adsorption separation unit in the first refined propylene-containing product.

In the case where the amount of MAPD in the first refined propylene-containing product approximates or slightly exceeds the allowable limit (for example, about 10 wppm), an MAPD, hydrogenation reactor may be optionally disposed between the depropanizer and the adsorption-desorption unit, whereby MAPD, which is neither separated nor removed by the depropanizer, is removed through a selective hydrogenation reaction, thus forming a second refined propylene-containing product, which may then be supplied into the adsorption separation unit. Here, at least about 90% (particularly, at least about 95%) of MAPD in the first refined propylene-containing product may be removed.

In an exemplary embodiment, the selective hydrogenation reaction may be carried out in the presence of a Group VIII metal, especially a Group VIII metal/support catalyst (metal content: for example, about: 0.01 to 1 wt %). Examples of the Group VIII metal may include Ru, Ph, Pd, Ir and Pt, and examples of the support may include inorganic oxide (particularly refractory inorganic oxide; such as alumina, silica-alumina and the like, activated carbon, etc. Furthermore, the selective hydrogenation reaction may be carried out at a temperature of, for example, about 50 to 100° C. (particularly about 60 to 80° C.) and a pressure of about 10 to 40 $kg/cm^2$ (particularly about 15 to 35 $kg/cm^2$).

In the case where the olefin compound in the C4+ hydrocarbon is removed through the hydrogenation reaction, propylene may also be hydrogenated during the hydrogenation reaction and may thus be lost. Hence, it is noted that the depropanizer cannot be replaced with the MAPD hydrogenation reactor.

In an exemplary embodiment, before the transfer of the propylene-containing product into the depropanizer, pressurization and/or cooling may be further performed in order to ensure stability of the depropanizer and the downstream processing unit, realize the operation conditions (temperature, pressure, etc.), and easily design the processing equipment size and material.

In an exemplary embodiment, dehydration and/or desulfurization may be further performed depending on the operation conditions after the dehydration reaction.

Downstream dehydration and/or desulfurization may be conducted in order to, for example, prevent the solidification of water due to cooling, prevent the deterioration of the adsorbing agent by water and a sulfur compound, and remove water and a sulfur compound for control of the quality of a propylene product. The position at which the dehydration and/or desulfurization are performed may be determined taking into consideration the dehydration and/or desulfurization conditions, investment costs and operating costs. For example, the unit therefore may be disposed downstream of the dehydration unit (and upstream of the depropanizer), or downstream of the depropanizer (and upstream of the olefin adsorption-desorption unit).

Meanwhile, in an exemplary embodiment, the propylene-containing product fed into the depropanizer may include hydrogen, methane, ethane, ethylene, carbon monoxide and/or carbon dioxide, each of which has a boiling point lower than that of propane. Such components are fed into the depropanizer and then moved toward the top thereof at a high rate, and may thus cause the performance of the depropanizer to deteriorate. Hence, before introduction of the propylene-containing product into the depropanizer, at least some of hydrogen, methane, C2 hydrocarbon (including, for example, ethane and ethylene), carbon monoxide and/or carbon dioxide may be optionally separated as the light gas stream. Here, the separation of the light gas stream is not particularly limited, but may be performed using at lease one selected from among a knock-out drum, a membrane, an adsorber, and a still.

The separation of the light gas stream may be conducted in order to improve the performance of the depropanizer while minimizing the processing investment and operation costs. In consideration thereof, excessively high separation performance may not be required, and small amounts of propane, propylene and C4+ may be further included in the light gas stream. In this case, recovering propylene that may be included in the light gas stream may be further performed as necessary. Also, additionally separating and recovering propane from the light gas stream may be optionally performed so that the propane may be subjected to dehydrogenation together with the propane-containing feedstock.

Propane-Propylene Separation through Selective Adsorption-Displacement Desorption of Propylene According to an embodiment of the present invention, the first refined propylene-containing product, which is the overhead stream of the depropanizer, is the stream including $H_2$, $CH_4$, and $C_3$ or smaller hydrocarbon (ethane, ethylene, propane and propylene), and is fed into the adsorption separation unit (olefin adsorption-desorption unit). The first refined propylene-containing product fed into the adsorption separation unit may contain, as impurities, water, nitrogen, carbon monoxide, carbon dioxide and/or a sulfur compound. Among such impurities, when the water and sulfur compound are fed into the zeolite-loaded adsorber, they may have a negative influence on the performance of the adsorption separation unit. For example, the sulfur compound may be chemically adsorbed to the pores and surface of the zeolite adsorbing agent to thus shorten the lifetime of the adsorbing agent, and the water may be strongly adsorbed to the pores and surface of the adsorbing agent to thus deteriorate the performance of the adsorbing agent. In an exemplary embodiment, if the concentrations of the water and sulfur compound, which are impurities of the first, refined propylene-containing product, approximate or exceed the allowable limit (for example, about 20 wppm), desulfurization and/or dehydration (removal of water or drying) may be additionally performed before the propane-propylene separation after the dehydrogenation reaction as described above.

In an exemplary embodiment, in order to prevent deterioration of the adsorbing agent, a guard bed may be disposed upstream of the adsorption separation unit. When the guard bed is provided in this way, at least one of gas components, for example, isobutylene, a sulfur compound, water, butadiene, carbon dioxide, and carbon monoxide, may be adsorbed and additionally removed.

The adsorption separation unit is not limited to a specific configuration, so long as propylene is selectively separated from the propylene-containing product. In an exemplary embodiment, the olefin adsorption-desorption unit may include at least two adsorbers filled with an adsorbing agent, a valve for adjusting the inner fluid stream of the unit, and the like. Particularly, at least, two adsorbers (filled with the adsorbing agent) connected in parallel are used, and individual adsorbers are switched between adsorption and desorption modes, thus enabling continuous operation. Here, in order to improve separation efficiency and yield, a cleaning process (or cleaning and recovery) may be further performed, in addition to the adsorption and desorption processes in individual adsorbers (for example, adsorption-cleaning-desorption, or adsorption-recovery-cleaning-desorption.

Moreover, the desorption process for recovering propylene may be performed in a displacement desorption manner using a desorbing agent. In some cases, a slight pressure drop may occur during the desorption process. The adsorption separation unit is exemplified by a separator as disclosed in Korean Patent application Publication No. 2012-33368, the disclosure of which is hereby incorporated in its entirety into this application.

In an exemplary embodiment, the operation of each of the adsorbers (four adsorbers) in the adsorption separation unit may be performed as shown in Table 3 below.

TABLE 3

| Adsorber 1 | Adsorption | Recovery | Cleaning | Desorption |
| Adsorber 2 | Desorption | Adsorption | Recovery | Cleaning |
| Adsorber 3 | Cleaning | Desorption | Adsorption | Recovery |
| Adsorber 4 | Recovery | Cleaning | Desorption | Adsorption |

In this embodiment, the kind of adsorbing agent is not particularly limited, so long as it is able to selectively adsorb olefin, among an olefin component and a paraffin component. Examples of the useful adsorbing agent may include π-complex for forming a π-complexation, zeolite X (for example, U.S. Pat. No. 2,882,244), and zeolite Y (for example, U.S. Pat. No. 3,130,007), which may be used alone or in combination. Particularly useful is zeolite X.

The adsorption process using a π-complex adsorbing agent is performed according to a principle for forming a complexation between a metal and an olefin. When the metal ion is a silver (Ag) ion, the empty outermost 5s orbital of Ag(I) accepts π-electrons from the 2p bond orbital of olefin so that a bonding is formed between the metal ion and the olefin, and simultaneously, electrons are provided from the 4d orbital of an Ag ion occupied with electrons into the empty π* 2p non-bond orbital of olefin to thus form π-bonding. The π-complex bonding force is about 4 to 15 kcal, stronger than van der Waals force mainly occurring upon physical adsorption, thereby ensuring high selectivity to olefin.

Also, zeolite X and Y are known to be a molecular sieve formed of inorganic oxide such as silica and alumina (i.e. aluminosilicate). Due to the macrocrystalline molecular sieve structure of zeolite, ability to selectively adsorb an olefin component may be obtained. As the adsorbing agent, zeolite particles are mixed with a binder component (for example, clay or alumina) and may then be extruded. In some cases, zeolite may be ion-exchanged or modified with alkali metal or alkaline earth metal.

In an embodiment of the present invention, the adsorber may be typically operated in a gaseous phase under appropriate temperature and pressure conditions therein. For example, the adsorption temperature may be set to the range of about 70 to 140° C., and particularly about 80 to 110° C. Also, the pressure may be determined taking into consideration ail of the given temperature, device size and material. If the pressure is too low, excessively large-sized pipes or equipment may be required. On the other hand, if the pressure is too high, limitations are imposed on determining the material. Hence, the pressure may fall in the range of, for example, about 5 to 40 kgf/cm$^2$, and particularly about 10 to 30 kgf/cm$^2$. Furthermore, the weight hourly space velocity (WHSV) of feedstock of the adsorber may fall in the range of, for example, about 0.3 to 5 hr$^{-1}$, and particularly about 0.5 to 1.5 hr$^{-1}$. The specific numeric ranges of the processing conditions in the adsorber are exemplary, and the present invention is not necessarily limited thereto, and the processing of the invention may be favorably performed under low temperature conditions compared to conventional techniques.

In the adsorption process, the first refined propylene-containing product may be fed upward from the bottom of the adsorber. The olefin component may be selectively adsorbed to the pores and surface of the adsorbing agent loaded in the adsorber, whereas the paraffin component is not substantially adsorbed but is discharged from the top of the adsorber. In some cases, it may be primarily heated using a heat exchanger or a heater and then fed into the adsorber. The propane-rich stream is separated by the adsorption process, and the propane-rich stream may further include a desorbing agent, present with the adsorbing agent in the previous desorption process, in addition to $H_2$, $CH_4$, and $C_3$ or smaller paraffin hydrocarbons of the first refined propylene-containing product.

In an exemplary embodiment, respective amounts of propane and fuel gas (methane and ethane) may be, for example, about 20 to 50 wt % (particularly, about 30 to 40 wt %) and about 1 to 10 wt % (particularly, about 1 to 5 wt %). Furthermore, the amount of the desorbing agent may be, for example, about 40 to 70 wt % (particularly, about 50 to 60 wt %). In addition, small amounts of nitrogen, carbon monoxide, carbon dioxide and sulfur compounds may be contained, and in some cases, propylene that is not completely separated may also be contained in a small amount.

In an embodiment of the present invention, after the termination of the adsorption process, the olefin component contained in the adsorbing agent is subjected to displacement desorption using a desorbing agent. To this end, used as the desorbing agent may be a hydrocarbon having a higher boiling point (a large molecular weight) than that of the C3 hydrocarbon. This process is performed in a displacement desorption manner in which the previously adsorbed materials are desorbed while the desorbing agent is adsorbed instead of the olefin component adsorbed to the adsorbing agent. The desorbing agent, may be a component in which the number of carbon atoms is higher than that of the adsorbed olefin component, especially a paraffin-based desorbing agent. For example, the desorbing agent may be a C4 hydrocarbon (particularly i-butane, n-butane or a mixture thereof) or a C4 hydrocarbon-rich fraction (the amount of C4 hydrocarbon is at least about 80 wt %, and particularly about 90 wt %).

The desorbing agent is fed to the bottom from the top of the adsorber (a kind of concurrent purging), and the propylene-rich stream containing the desorbed olefin component (ethylene and propylene) and the desorbing agent component is discharged as the bottom stream. Consequently, respective amounts of propylene and ethylene in the propylene-rich stream may be, for example, about 30 to 60 wt % (particularly, about 35 to 45 wt %) and about 1 wt % or less. Also, the amount of the deserting agent may be, for example, about 40 to 70 wt % (particularly, about 50 to 60 wt %).

The displacement desorption process is favorably performed under isobaric conditions that do not need pressure fluctuation or under conditions that need only slight pressure fluctuations, as in the conventional PSA process.

Recovery of Propylene and Recycling of Propane

In an exemplary embodiment, the propane-rich stream is transferred into a propane splitter, whereby a gas mixture containing $H_2$, $CH_4$, $C_2H_6$; and $C_3H_8$ is separated as the overhead stream and the desorbing agent is separated as the bottom stream. Here, the propane splitter may be operated at a pressure of, for example, about 20 to 35 kgf/cm$^2$ (more particularly, about 25 to 30 kgf/cm$^2$) and a temperature of about 40 to 80° C. (more particularly, about 50 to 70° C.) at the top thereof and a temperature of about 90 to 140° C. (more particularly, about 110 to 135° C.) at the bottom thereof. Furthermore, the number of trays of the propane splitter may be, for example, about 70 to 110 (particularly, about 80 to 100). The propane-rich stream from which the desorbing agent is separated may be split into $C_3H_8$, fuel gas ($CH_4$ and $C_2H_6$) and hydrogen using a separation process known in the art, for example, distillation, PSA (pressure swing adsorption), membrane separation or a combination thereof, and the separated propane may be recycled and fed into the dehydrogenation reactor together with the propane-containing feedstock. The PSA separation is described in Knaebel et al, "Pressure swing adsorption", Wiley-VCH, (1994), and the membrane separation is described in, for example, U.S. Pat. No. 4,589,896. These documents are incorporated by reference into this application.

Meanwhile, the propylene-rich stream may contain, in addition to propylene (C3=), ethylene (C2=) and the desorbing agent, and in some cases, a very small amount of acetylene. The propylene-rich stream may be optionally separated using an ethylene splitter so that off-gas (for example, ethylene, particularly ethylene and a trace of acetylene) may be separated as the overhead stream and the bottom stream containing propylene and the desorbing agent may be separated. The stream containing propylene and the desorbing agent is transferred into the propylene splitter, whereby the overhead stream comprising propylene and the bottom stream comprising the desorbing agent may be separated from each other. In this way, when the ethylene splitter is disposed upstream of the propylene splitter, propylene of high purity (for example, about 99% or more, particularly about 99.5% or more, and more particularly about 99.8% or more) may be recovered.

Here, the ethylene splitter may be operated at a pressure of, for example, about 20 to 35 kgf/cm$^2$ (more particularly, about 25 to 30 kgf/cm$^2$) and a temperature of about 30 to 70° C. (more particularly, about 40 to 60° C.) at the top thereof and of about 80 to 110° C. (more particularly, about 90 to 100° C.) at the bottom thereof. Also, the propylene splitter may be operated at a pressure of, for example, about 20 to 35 kgf/cm$^2$ (more particularly, about 25 to 30 kgf/cm$^2$) and a temperature of about 40 to 80° C. (more particularly, about 50 to 70° C.) at the top thereof and of about 90 to 140° C. (more particularly, about 110 to 135° C.) at the bottom thereof. Furthermore, the number of trays of each of the ethylene splitter and the propylene splitter may be, for example, about 15 to 45 (particularly, about 30 to 50) and about 60 to 100 (particularly, about 70 to 90), respectively.

Recycling of Desorbing Agent

In an embodiment of the present invention, the desorbing agent separated from each of the propane-rich stream and the propylene-rich stream is recovered and may then be recycled to the olefin adsorption-desorption unit. Here, in the course of transferring the recycled desorbing agent stream into the olefin adsorption-desorption unit, a makeup-desorbing agent may be supplemented. In some cases, the desorbing agent is dried, and may then be fed into the olefin adsorption-desorption unit after having been heated at, for example, about 70 to 100° C. (gaseous phase).

Meanwhile, the C4+ fraction separated as the bottom stream of the depropanizer may contain, in addition to butane (isobutane and n-butane), isobutylene, 1-butene and 1-pentene, and small amounts of 1,3-butadiene and BTX. Thus, in an exemplary embodiment, high-value-added BTX may be additionally separated and recovered using a still or the like.

Figure 3:
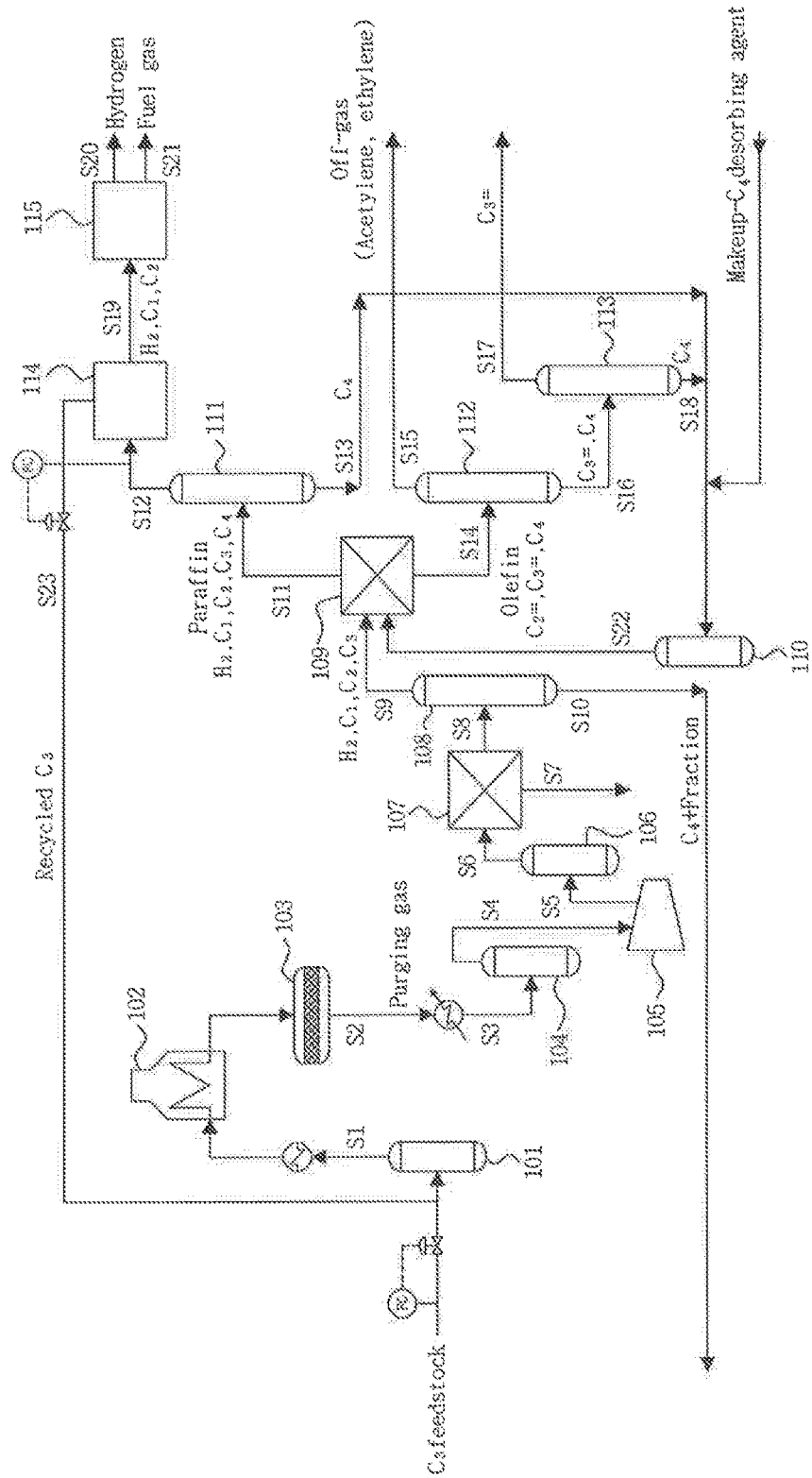
FIG. 3 shows a process of separating propylene from a dehydrogenation product of propane-containing feedstock using a depropanizer and an adsorption separation unit (an olefin adsorption-desorption unit) according to an embodiment of the present invention.

FIG. 3 shows a process of separating propylene from the dehydrogenation product of propane-containing feedstock according to an embodiment of the present invention.

In this embodiment, the propane-containing feedstock is fed into a feedstock evaporator 101 in a state of being combined with propane recycled in the previous mode. The feedstock S1 evaporated in the feedstock evaporator is subjected to heat exchange, fed into a feedstock heater 102, heated to about 500 to 700° C. (particularly about 550 to 650° C.), and transferred into a dehydrogenation reactor 103 so that propane in the feedstock is converted into propylene through a dehydrogenation reaction. As such, side reactions may also occur.

The propylene-containing product S2 (gaseous phase) discharged from the dehydrogenation reactor 103 is moved along the gas stream, and is selectively purged with a purging gas (for example, steam gas) (for example, most of the propylene-containing product is transferred along the gas stream, and some of the dehydration product present in the reactor may be transferred through purging), and is then cooled to about 25 to 50° C. (particularly, about 30 to 40° C., and more particularly about 35° C.) through heat exchange. The purging gas may be exemplified by an inert gas such as nitrogen, in addition to the steam gas, or a gas mixture comprising steam and inert gas. The cooled propylene-containing product S3 is transferred to a compressor suction drum 104 to remove a liquid component. Thereafter, the propylene-containing product stream S4 in a gaseous phase passed through the compressor suction drum 104 is fed into a compressor 105 and thus pressurized (for example, from about 0.3 to 1 kg/cm$^2$ to about 20 to 35 kg/cm$^2$. The compressed propylene-containing product stream S5 is transferred to a reaction product dryer knock-out drum 106 and the pressure is controlled so that the downstream separation process may be carried out at room temperature. The propylene-containing product 36 in which the pressure is controlled as above is fed into a product gas dryer 107 so that the remaining water S7 is removed.

The dewatered product stream S8 (for example, water content of about 20 wppm or less) is transferred to a depropanizer 108, thereby obtaining, as the overhead stream S9, a first refined propylene-containing product stream containing hydrogen, methane, and C3 or smaller hydrocarbons. Meanwhile, the bottom stream S10 of the depropanizer 108 contains C4+ fractions, for example, butadiene ($C_4H_6$), isobutylene (i-$C_4H_8$), 1-butene (1-$C_4H_8$), c-2-butene, t-2-butene, pentene, benzene, toluene and xylene. Also, a portion of methylacetylene-propadiene (MAPD) present in a very small amount, in the product may be incorporated into the bottom stream during the separation process.

In an exemplary embodiment, the bottom stream S10 separated from the depropanizer 108 contains not only the C4 hydrocarbon but also high-value-added components such as benzene, toluene and xylene (BTX). To this end, the bottom stream S10 is optionally transferred to a debutanizer (not shown), and is thus split into a C4 product (especially, C4 olefin or diolefin) stream and a C5+ product stream, from which desired components may be recovered.

The overhead stream S9 of the depropanizer 108, mainly containing hydrogen and C3 or smaller hydrocarbon, is fed into an olefin adsorption-desorption unit 109. Here, the overhead stream S9 is passed through the adsorbing agent, whereby only the olefin component is selectively adsorbed to the adsorbing agent. On the other hand, the hydrogen and paraffin-based hydrocarbon in the stream S9 are not adsorbed but pass through the adsorbing agent. Accordingly, the propane-rich stream S11 is discharged during the adsorption process. The adsorbing agent contains the desorbing agent (particularly, the C4 paraffin-based desorbing agent) used in the previous propylene desorption mode, and thus the propane-rich stream S11 contains not only the hydrogen and C3 or smaller paraffin-based hydrocarbon, but also the desorbing agent. The paraffin-rich stream S11 is delivered to a propane splitter 111, and is thus split into the overhead stream 512, containing the hydrogen and C3 or smaller paraffin-based hydrocarbon, and the bottom stream S13, containing the desorbing agent.

After the completion of the adsorption process, the processing is switched into the olefin desorption process through the desorption process, namely displacement desorption. In addition to the basic processes of adsorption and desorption, additional, processing for increasing the separation level, and yield, for example a cleaning process, may be further performed. Through the desorption process, the propylene-rich stream S14 is discharged, and the stream S14 contains not only ethylene and propylene but also the desorbing agent (particularly a C4 paraffin-based desorbing agent). Thereafter, the stream S14 is delivered to an ethylene splitter 112, and is thus split into the overhead stream S15 containing off-gas (including ethylene and a trace of acetylene), and the bottom stream S16 containing propylene and the desorbing agent is discharged. Thereafter, the bottom stream S16 is delivered to a propylene splitter 113 and thus split into the overhead stream S17 containing propylene and the bottom stream S18 containing the desorbing agent.

The propylene-rich stream separated from the olefin adsorption-desorption unit 109 is fed to the propylene splitter via the ethylene splitter, whereby the purity of the recovered propylene product may be increased to about 99% or more, particularly 99.5% or more, and more particularly 99.6% or more. The desorbing agent-containing stream S18 separated from the propylene splitter is recycled to the olefin adsorption-desorption unit 109 through a desorbing agent drum 110, and is thus used as the desorbing agent.

Meanwhile, the overhead stream S12 discharged from the propane splitter 111 is fed to a first PSA unit 114, and the first PSA unit functions to selectively adsorb only propane under pressurization (for example, about 15 to 30 kg/cm$^2$) and enables hydrogen, and fuel gas (methane and ethane) to pass therethrough. Thereafter, as the pressure is reduced, propane may be recovered, and the separated propane S23 has a purity of, for example, at least about 90 wt %, and is recycled and fed to the feedstock evaporator 101 together with the propane-containing feedstock S1.

The stream S19 containing hydrogen and fuel gas is delivered to a second PSA unit (pressurization conditions: for example, about 15 to 30 kg/cm$^2$) and is thus split into high-purity hydrogen and fuel gas, which are then recovered. The high-purity hydrogen (having, for example, a purity of at least about 90 mol %) may be provided as the hydrogen source when the hydrogenation process (not shown) of MAPD contained in the overhead stream of the depropanizer 108 is optionally performed. Also, the desorbing agent-containing stream discharged as the bottom stream S13 of the propane splitter 111 is recycled to the olefin adsorption-desorption unit 109 via the desorbing agent drum 110 and is thus used as the desorbing agent.

The first PSA unit and the second PSA unit are used to separate hydrogen, fuel gas and propane gas from the gas mixture of the overhead stream S12 of the propane splitter 111, but the separation process is not limited to PSA. At least one of PSA, membrane separation, distillation and adsorption may be understood as being performed.

A better understanding of the present invention may be obtained through the following Examples which are set forth to illustrate, but are not to be construed to limit the scope of the present invention.

EXAMPLE 1

As shown in FIG. 2, the propane-containing feedstock was subjected to dehydrogenation, and propylene was separated and recovered. Here, as a C4 desorbing agent used for displacement desorption in an adsorption-desorption unit (adsorber), a mixture of i-butane and n-butane (4:6) was used. The operation conditions of a dehydrogenation reactor 103, a depropanizer 108, an olefin adsorption-desorption unit 109, a propane splitter 111, an ethylene splitter 112 and a propylene splitter 113 during the processing are shown in Tables 4 to 9 below (after dehydrogenation, a purging gas composed of steam was fed at 10,395 kg/hr).

TABLE 4

| Dehydrogenation reactor | | Unit | Conditions | Note |
|---|---|---|---|---|
| Pressure | Inlet | kg/cm2 G | 0.15 | |
| | Outlet | kg/cm2 G | −0.53 | |
| Temperature | Inlet | ° C. | 600 | |
| | Outlet | ° C. | 595 | |
| Feedstock fed into reactor | Fresh feedstock | kg/hr | 91,690 | |
| | Recycled propane | kg/hr | 119,019 | |
| | Total | kg/hr | 210,709 | S1 |
| C3 in feedstock fed into reactor | Propane in feedstock | wt % | 95 | |
| | Recycled propane | wt % | 93.7 | |
| | total | wt % | 94.3 | S1 |

TABLE 5

| Depropanizer | | | | |
|---|---|---|---|---|
| | | Unit | Conditions | Note |
| Temperature | Top | ° C. | 61 | |
| | Bottom | ° C. | 137 | |
| Pressure | Top | kg/cm2 G | 29.1 | |
| | Bottom | kg/cm2 G | 29.7 | |
| Separation | C4 olefin content in overhead stream | wt % | 0.063 | S9 < 0.2 wt % |
| Tray | Number of trays | ea | 150 | Efficiency = 100% |

TABLE 6

| Olefin adsorption-desorption unit | | |
|---|---|---|
| | Unit | Conditions |
| Pressure | kg/cm2 G | 28.50 |
| Temperature | ° C. | 105 |

TABLE 7

| Propane splitter | | | | |
|---|---|---|---|---|
| | | Unit | Conditions | Note |
| Temperature | Top | ° C. | 62 | |
| | Bottom | ° C. | 129 | |
| Pressure | Top | kg/cm2 G | 28 | |
| | Bottom | kg/cm2 G | 28.4 | |
| Separation | C3 in overhead stream | wt % | 83.66 | S12 |
| | C4 in bottom stream | wt % | 99.99 | S13 |
| Configuration | Number of trays | ea | 90 | Efficiency = 100% |

TABLE 8

Ethylene splitter

|  |  | Unit | Conditions | Note |
|---|---|---|---|---|
| Temperature | Top | ° C. | 52 | |
|  | Bottom | ° C. | 96 | |
| Pressure | Top | kg/cm2 G | 28.0 | |
|  | Bottom | kg/cm2 G | 28.3 | |
| Separation | C3 in overhead stream | wt % | 0.08 | S16 |
| Configuration | Number of trays | ea | 30 | Efficiency = 70% |

TABLE 9

Propylene splitter

|  |  | Unit | Conditions | Note |
|---|---|---|---|---|
| Temperature | Top | ° C. | 62 | |
|  | Bottom | ° C. | 126 | |
| Pressure | Top | kg/cm2 G | 26.3 | |
|  | Bottom | kg/cm2 G | 26.7 | |
| Separation | C3= | wt % | 99.80 | S17 |
|  | C4 in bottom stream | wt % | 99.99 | S18 |
| Configuration | Number of trays | ea | 80 | Efficiency = 100% |

Also, the compositions of the feedstock and individual streams were analyzed. The results are shown in Tables 10 to 13 below.

TABLE 10

|  |  | Unit | Feed | | | | |
|---|---|---|---|---|---|---|---|
|  |  |  | S1 | S2 | S3 | S4 | S5 |
|  |  |  | Pressure | | | | |
|  |  | KG/CM2G | 3.7 | −0.5 | −0.5 | −0.7 | 30.0 |
|  |  |  | Temp. | | | | |
|  | Component | M.W. | 15.0 LIQUID | 450.0 VAPOR | 595.0 VAPOR | 595.0 VAPOR | 35.0 VAPOR | 85.8 VAPOR |
| 1 | H2O | 18.02 kg/hr | | | 2,311.8 | 8,564.2 | 8,564.2 | 550.9 |
| 2 | H2 | 2.02 kg/hr | | | 4,249.9 | 4,249.9 | 4,249.9 | 4,249.9 |
| 3 | N2 | 28.01 kg/hr | | | | 1,953.2 | 1,953.2 | 1,953.2 |
| 4 | CO | 28.01 kg/hr | | | | 1,845.9 | 1,845.9 | 1,845.9 |
| 5 | CO2 | 44.01 kg/hr | | | | 343.4 | 343.4 | 343.4 |
| 6 | H2S | 34.08 kg/hr | | | | | | |
| 7 | Cl | 16.04 kg/hr | | | 2,082.0 | 2,082.0 | 2,082.0 | 2,082.0 |
| 8 | ACETYLENE | 26.04 kg/hr | | | 21.5 | 21.5 | 21.5 | 21.5 |
| 9 | ETHYLENE | 28.05 kg/hr | | | 601.0 | 601.0 | 601.0 | 601.0 |
| 10 | ETHANE | 30.07 kg/hr | 1,247.1 | 1,247.1 | 3,735.8 | 3,735.8 | 3,735.8 | 3,735.8 |
| 11 | PROPYNE | 40.07 kg/hr | | | | | | |
| 12 | PROPDIEN | 40.07 kg/hr | | | 1.0 | 1.0 | 1.0 | 1.0 |
| 13 | PROPENE | 42.08 kg/hr | 871.1 | 880.0 | 74,986.0 | 74,986.0 | 74,986.0 | 74,986.0 |
| 14 | PROPANE | 44.10 kg/hr | 87,150.9 | 198,121.2 | 111,469.1 | 111,469.1 | 111,469.1 | 111,469.1 |
| 15 | IBUTANE | 58.12 kg/hr | 1,898.2 | 8,823.2 | 7,712.5 | 7,712.5 | 7,712.5 | 7,712.5 |
| 16 | IBUTENE | 56.11 kg/hr | | 11.0 | 1,072.0 | 1,072.0 | 1,072.0 | 1,072.0 |
| 17 | NBUTANE | 58.12 kg/hr | 522.7 | 1,123.3 | 864.0 | 864,0 | 864.0 | 864.0 |
| 18 | 1BUTENE | 56.11 kg/hr | | 0.7 | 208.4 | 208.4 | 208.4 | 208.4 |
| 19 | BUTADIENE | 54.09 kg/hr | | 0.0 | 69.6 | 69.6 | 69.6 | 69.6 |
| 20 | 1PENTENE | 70.13 kg/hr | | | 196.3 | 196.3 | 196.3 | 196.3 |
| 21 | BENZENE | 78.11 kg/hr | | | 108.4 | 108.4 | 108.4 | 108.4 |
| 22 | TOLUENE | 92.14 kg/hr | | | 150.3 | 150.3 | 150.3 | 105.3 |
| 23 | PXYLENE | 106.17 kg/hr | | | 386.4 | 386.4 | 386.4 | 386.4 |

TABLE 11

|  |  | Unit | S6 | S7 | S8 | S9 | S10 | S11 |
|---|---|---|---|---|---|---|---|---|
|  |  |  | Pressure | | | | | |
|  |  | KG/CM2G | 30.0 | | 29.4 | 28.5 | | 28.2 |
|  |  |  | Temp. | | | | | |
|  | Component | M.W. | 85.8 VAPOR | 85.8 WATER | 85.8 VAPOR | 43.8 VAPOR | 136.5 LIQUID | 68.0 MIXED |
| 1 | H2O | 18.02 kg/hr | 550.9 | 550.9 | | | | |
| 2 | H2 | 2.02 kg/hr | 4,249.9 | | 4,249.9 | 4,249.9 | | 4,249.9 |
| 3 | N2 | 28.01 kg/hr | 1,953.2 | | 1,953.2 | 1,953.2 | | 1,953.2 |
| 4 | CO | 28.01 kg/hr | 1,845.9 | | 1,845.9 | 1,845.9 | | 1,845.9 |
| 5 | CO2 | 44.01 kg/hr | 343.4 | | 343.4 | 343.4 | | 343.4 |
| 6 | H2S | 34.08 kg/hr | | | | | | |
| 7 | Cl | 16.04 kg/hr | 2,082.0 | | 2,082.0 | 2,082.0 | | 2,082.0 |
| 8 | ACETYLENE | 26.04 kg/hr | 21.5 | | 21.5 | 21.5 | 0.0 | 0.0 |

TABLE 11-continued

| | Unit | S6 | S7 | S8 | S9 | S10 | S11 |
|---|---|---|---|---|---|---|---|
| | | | | Pressure | | | |
| | KG/CM2G | 30.0 | | 29.4 | 28.5 | | 28.2 |
| | | | | Temp. | | | |
| | | 85.8 | 85.8 | 85.8 | 43.8 | 136.5 | 68.0 |
| Component | M.W. | VAPOR | WATER | VAPOR | VAPOR | LIQUID | MIXED |
| 9 ETHYLENE | 28.05 kg/hr | 601.0 | | 601.0 | 601.0 | 0.0 | 0.0 |
| 10 ETHANE | 30.07 kg/hr | 3,735.8 | | 3,735.8 | 3,735.8 | 0.0 | 3,735.8 |
| 11 PROPYNE | 40.07 kg/hr | | | | | | |
| 12 PROPDIEN | 40.07 kg/hr | 1.0 | | 1.0 | 1.0 | 0.0 | 0.2 |
| 13 PROPENE | 42.08 kg/hr | 74,986.0 | | 74,986.0 | 74,986.0 | 0.0 | 8.9 |
| 14 PROPANE | 44.10 kg/hr | 111,469.1 | | 111,469.1 | 111,469.1 | 0.0 | 111,479.3 |
| 15 IBUTANE | 58.12 kg/hr | 7,712.5 | | 7,712.5 | 5,136.2 | 2,576.4 | 71,546.6 |
| 16 IBUTENE | 56.11 kg/hr | 1,072.0 | | 1,072.0 | 121.8 | 950.2 | 220.5 |
| 17 NBUTANE | 58.12 kg/hr | 864.0 | | 864.0 | 0.0 | 864.0 | 103,333.3 |
| 18 1BUTENE | 56.11 kg/hr | 208.4 | | 208.4 | 9.1 | 199.2 | 16.5 |
| 19 BUTADIENE | 54.09 kg/hr | 69.6 | | 69.6 | 0.0 | 69.6 | 0.0 |
| 20 1PENTENE | 70.13 kg/hr | 196.3 | | 196.3 | 0.0 | 196.3 | |
| 21 BENZENE | 78.11 kg/hr | 108.4 | | 108.4 | | 108.4 | |
| 22 TOLUENE | 92.14 kg/hr | 150.3 | | 150.3 | | 150.3 | |
| 23 PXYLENE | 106.17 kg/hr | 386.4 | | 386.4 | | 386.4 | |

TABLE 12

| | Unit | S12 | S13 | S14 | S15 | S16 | S17 |
|---|---|---|---|---|---|---|---|
| | | | | Pressure | | | |
| | KG/CM2G | 27.4 | | 28.2 | 27.4 | | |
| | | | | Temp. | | | |
| | | 37.7 | 129.4 | 105.0 | 20.0 | 45.0 | 38.0 |
| Component | M.W. | VAPOR | LIQUID | VAPOR | VAPOR | LIQUID | LIQUID |
| 1 H2O | 18.02 kg/hr | | | | | | |
| 2 H2 | 2.02 kg/hr | 4,249.9 | | | | | |
| 3 N2 | 28.01 kg/hr | 1,953.2 | | | | | |
| 4 CO | 28.01 kg/hr | 1,845.9 | | | | | |
| 5 CO2 | 44.01 kg/hr | 343.4 | 0.0 | | | | |
| 6 H2S | 34.08 kg/hr | | | | | | |
| 7 Cl | 16.04 kg/hr | 2,082.0 | | | | | |
| 8 ACETYLENE | 26.04 kg/hr | | | 21.5 | 14.5 | 6.2 | 6.2 |
| 9 ETHYLENE | 28.05 kg/hr | | | 601.0 | 446.3 | 133.4 | 133.4 |
| 10 ETHANE | 30.07 kg/hr | 3,735.8 | 0.0 | 0.0 | 0.0 | 0.0 | 0.0 |
| 11 PROPYNE | 40.07 kg/hr | | | | | | |
| 12 PROPDIEN | 40.07 kg/hr | 0.2 | 0.0 | 1.2 | 0.0 | 1.2 | 0.8 |
| 13 PROPENE | 42.08 kg/hr | 8.9 | 0.0 | 74,991.8 | 304.5 | 74,643.6 | 74,629.2 |
| 14 PROPANE | 44.10 kg/hr | 111,462.7 | 16.7 | 6.6 | 0.0 | 6.6 | 6.6 |
| 15 IBUTANE | 58.12 kg/hr | 6,932.7 | 64,613.9 | 42,971.4 | 0.1 | 42,971.3 | 0.0 |
| 16 IBUTENE | 56.11 kg/hr | 11.0 | 209.5 | 264.5 | 0.0 | 264.5 | 0.0 |
| 17 NBUTANE | 58.12 kg/hr | 602.6 | 102,730.7 | 66,862.7 | 0.1 | 66,862.6 | 0.0 |
| 18 1BUTENE | 56.11 kg/hr | 0.7 | 15.9 | 19.8 | 0.0 | 19.8 | 0.0 |
| 19 BUTADIENE | 54.09 kg/hr | 0.0 | 0.0 | 0.0 | 0.0 | 0.0 | 0.0 |
| 20 1PENTENE | 70.13 kg/hr | | | 0.0 | | | |
| 21 BENZENE | 78.11 kg/hr | | | | | | |
| 22 TOLUENE | 92.14 kg/hr | | | | | | |
| 23 PXYLENE | 106.17 kg/hr | | | | | | |

TABLE 13

| | Unit | S18 | S19 | S20 | S21 | S22 | S23 |
|---|---|---|---|---|---|---|---|
| | | | | Pressure | | | |
| | KG/CM2G | | 26.2 | 25.0 | 25.0 | | |
| | | | | Temp. | | | |
| | | 125.8 | 38.7 | 39.7 | 39.7 | 105.0 | 38.7 |
| Component | M.W. | LIQUID | VAPOR | VAPOR | VAPOR | LIQUID | LIQUID |
| 1 H2O | 18.02 kg/hr | | | | | | |
| 2 H2 | 2.02 kg/hr | | 4,249.9 | 4,249.9 | | | |
| 3 N2 | 28.01 kg/hr | | 1,953.2 | | 1,953.2 | | |
| 4 CO | 28.01 kg/hr | | 1845.9 | | 1,845.9 | | |

TABLE 13-continued

| | Unit | S18 | S19 | S20 | S21 | S22 | S23 |
|---|---|---|---|---|---|---|---|
| | | | | Pressure | | | |
| | KG/CM2G | | 26.2 | 25.0 | 25.0 | | |
| | | | | Temp. | | | |
| Component | M.W. | 125.8 LIQUID | 38.7 VAPOR | 39.7 VAPOR | 39.7 VAPOR | 105.0 LIQUID | 38.7 LIQUID |
| 5 CO2 | 44.01 kg/hr | | 343.4 | | 343.4 | | |
| 6 H2S | 34.08 kg/hr | | | | | | |
| 7 C1 | 16.04 kg/hr | | 2,082.0 | | 2,082.0 | | |
| 8 ACETYLENE | 26.04 kg/hr | 0.0 | | | | 0.0 | |
| 9 ETHYLENE | 28.05 kg/hr | 0.0 | | | | 0.0 | |
| 10 ETHANE | 30.07 kg/hr | | 3,735.8 | | 3,735.8 | 0.0 | |
| 11 PROPYNE | 40.07 kg/hr | | | | | | |
| 12 PROPDIEN | 40.07 kg/hr | 0.3 | 0.2 | | 0.2 | 0.3 | |
| 13 PROPENE | 42.08 kg/hr | 14.4 | | | | 14.6 | 8.9 |
| 14 PROPANE | 44.10 kg/hr | 0.0 | | | | 16.8 | 111,462.7 |
| 15 IBUTANE | 58.12 kg/hr | 42,971.2 | | | | 109,381.8 | 6,932.7 |
| 16 IBUTENE | 56.11 kg/hr | 264.5 | | | | 363.1 | 11.0 |
| 17 NBUTANE | 58.12 kg/hr | 66,862.6 | | | | 170,196.0 | 602.6 |
| 18 1BUTENE | 56.11 kg/hr | 19.8 | | | | 27.2 | 0.7 |
| 19 BUTADIENE | 54.09 kg/hr | 0.0 | | | | 0.0 | 0.0 |
| 20 1PENTENE | 70.13 kg/hr | | | | | | 0.0 |
| 21 BENZENE | 78.11 kg/hr | | | | | | |
| 22 TOLUENE | 92.14 kg/hr | | | | | | |
| 23 PXYLENE | 106.17 kg/hr | | | | | | |

TABLE 14

| Product | Unit | Produced amount | Note |
|---|---|---|---|
| Propylene | kg/hr | 74,776 | S17 |
| C4+ | kg/hr | 5,501 | S10 |
| Hydrogen | kg/hr | 4,250 | S20 |
| Fuel gas | kg/hr | 9,961 | S21 |
| Off-gas | kg/hr | 766 | S15 |
| Water | kg/hr | 8,564 | S7 & compressor |
| Total | kg/hr | 103,817 | |

As is apparent from the above Tables, the concentration of propylene in the stream S17 was about 99.8%. Thereby, high-purity propylene satisfying a polymer-grade propylene standard (99.5% or more) can be separated from the dehydrogenation product of propane-containing feedstock even without the use of a conventional cooling separation process and a C3 product splitter, and the investment costs of the total processing and energy can be reduced. In particular, the depropanizer is disposed upstream of the adsorption-desorption unit, thus effectively removing components that adversely affect the adsorbing agent of the adsorption-desorption unit.

Accordingly, simple modifications or variations of the present invention may be easily performed by those skilled in the art, and may fail within the scope of the present invention.

The invention claimed is:

1. A method of separating propylene from a dehydrogenation product of a propane-containing feedstock, comprising the steps of:
   a) providing a propylene-containing product obtained by dehydrogenating the propane-containing feedstock, the propylene-containing product containing 25 to 50 wt % of propylene, 40 to 65 wt % of propane and 1 to 8 wt % of a C4+ hydrocarbon, an amount of isobutylene in the C4+ hydrocarbon being 0.1 to 2 wt % based on an amount of the propylene-containing product;
   b) transferring the propylene-containing product to a depropanizer so that at least a portion of the C4+ hydrocarbon is separated as a bottom stream and a first refined propylene-containing product is separated as an overhead stream;
   c) transferring the first refined propylene-containing product to an adsorption separation unit so as to be split into (i) a propane-rich stream and (ii) a propylene-rich stream through selective adsorption-desorption of olefin, wherein the propane-rich stream contains propane, hydrogen, methane, ethane and a desorbing agent;
   d) separating and recovering propylene from the propylene-rich stream;
   e) separating the propane-rich stream into a top stream and a bottom stream by using a propane splitter, wherein the top stream comprises the hydrogen, methane, ethane, and propane and the bottom stream comprises the desorbing agent, wherein the propane separated from the propane-rich stream is recycled to the step a), and is thereby dehydrogenated together with the propane-containing feedstock; and
   f) supplying the desorbing agent separated from the propane-rich stream to the step c).

2. The method of claim 1, wherein an amount of a C4 olefin compound in the C4+ hydrocarbon is 0.5 to 3 wt % based on the amount of the propylene-containing product, an amount of 1,3-butadiene in the C4+ hydrocarbon is 0.01 to 0.2 wt % based on the amount of the propylene-containing product, and an amount of benzene, toluene and xylene (BTX) in the C4+ hydrocarbon is 0.1 to 1 wt % based on the amount of the propylene-containing product.

3. The method of claim 1, further comprising pressurizing the propylene-containing product to 20 to 35 kg/cm$^2$, before the step b).

4. The method of claim 1, further comprising separating a light gas stream containing at least a portion of hydrogen, methane, a C2 hydrocarbon (including ethane and ethylene), carbon monoxide and carbon dioxide from the propylene-containing product, before the step b).

5. The method of claim 1, further comprising transferring the C4+ hydrocarbon separated in the step b) to a debutanizer so as to be split into a C4 hydrocarbon and a C5+ hydrocarbon.

6. The method of claim 5, further comprising separating and recovering benzene, toluene and xylene (BTX) from the C5+ hydrocarbon.

7. The method of claim 1, wherein the first refined propylene-containing product, contains hydrogen and a C3 or smaller hydrocarbon.

8. The method of claim 7, wherein in the first refined propylene-containing product, respective amounts of propylene and propane are 30 to 50 wt % and 40 to 65 wt %, and an amount of isobutylene is 0.3 wt % or less.

9. The method of claim 8, wherein in the first refined propylene-containing product, respective amounts of 1,3-butadiene-containing diolefin and BTX are 500 wppm or less and 100 wppm or less.

10. The method of claim 1, wherein a desorbing agent comprising a paraffin-based hydrocarbon having a larger number of carbon atoms than that of propylene is used in the absorption separation unit.

11. The method of claim 10, wherein the desorbing agent is a C4 hydrocarbon, or a C4 hydrocarbon-rich fraction.

12. The method of claim 1, wherein the depropanizer is operated at a temperature of 50 to 100° C. at a top thereof and a temperature of 120 to 150° C. at a bottom thereof under a pressure of 20 to 40 kg/cm$^2$, and a number of trays thereof is 100 to 170.

13. The method of claim 1, wherein the propane-rich stream from which the desorbing agent is separated is subjected to at least one separation process PSA (pressure swing adsorption) and membrane separation and is thus split into propane, fuel gas (methane and ethane) and hydrogen, and the separated propane is recycled to the step a).

14. The method of claim 1, wherein the propylene-rich stream contains, in addition to propylene, a desorbing agent, and the propylene is separated and recovered from the desorbing agent, and the separated desorbing agent is supplied to the step c).

15. The method of claim 14, wherein the propylene-rich stream contains ethylene, propylene and the desorbing agent, and is fed into an ethylene splitter so that off-gas containing ethylene is separated as an overhead stream and a bottom stream containing propylene and the desorbing agent is separated, and the bottom stream is transferred to a propylene splitter so that an overhead stream comprising propylene and a bottom stream comprising the desorbing agent are separated from each other, and the separated propylene is recovered and the separated desorbing agent is supplied to the step c).

16. The method of claim 1, wherein the first refined propylene-containing product contains MAPD (methylacetylene-propadiene), and MAPD that is not separated by the depropanizer is removed through selective hydrogenation between the steps b) and c), thus forming a second refined propylene-containing product, which is then fed to the adsorption separation unit.

17. A method of separating propylene from a dehydrogenation product of a propane-containing feedstock, comprising the steps of:
a) providing a propylene-containing product obtained by dehydrogenating the propane-containing feedstock, the propylene-containing product containing 25 to 50 wt % of propylene, 40 to 65 wt % of propane and 1 to 8 wt % of a C4+ hydrocarbon, an amount of isobutylene in the C4+ hydrocarbon being about 0.1 to 2 wt % based on an amount of the propylene-containing product;
b) cooling the propylene-containing product to 25 to 50° C. through heat exchange;
c) pressurizing the cooled propylene-containing product to 20 to 35 kg/cm$^2$ and performing drying;
d) transferring the pressurized and dried propylene-containing product to a depropanizer so that at least a portion of the C4+ hydrocarbon is separated as a bottom stream and a first refined propylene-containing product including hydrogen and a C3 or smaller hydrocarbon is separated as an overhead stream;
e) transferring the first refined propylene-containing product to an adsorption separation unit so as to be split into (i) a propane-rich stream containing hydrogen, a C3 or smaller paraffin-based hydrocarbon and a desorbing agent and (ii) a propylene-rich stream containing ethylene, propylene and the desorbing agent through selective adsorption-desorption of olefin; and
f) transferring the propane-rich stream to a propane splitter so that the desorbing agent is separated therefrom to give a propane-rich stream having no desorbing agent, supplying the separated desorbing agent to the step c), separating propane from the propane-rich stream having no desorbing agent to give a remaining stream having no propane, recycling the separated propane to the step a), and separating and recovering hydrogen and fuel gas from the remaining stream having no propane; and
g) separately from the step f), transferring the propylene-rich stream to an ethylene splitter so as to be split into an overhead stream including ethylene-containing off-gas and a bottom stream including propylene and the desorbing agent, transferring the stream including propylene and the desorbing agent to a propylene splitter to thus be split into propylene and the desorbing agent, recovering the separated propylene, and supplying the separated desorbing agent to the step e).

* * * * *